(12) United States Patent
Luber et al.

(10) Patent No.: US 6,258,381 B1
(45) Date of Patent: Jul. 10, 2001

(54) TABLET AND PROCESS FOR MAKING THE SAME

(75) Inventors: Joseph R. Luber, Quakertown, PA (US); Frank J. Bunick, Randolph, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/502,594

(22) Filed: Feb. 11, 2000

(51) Int. Cl.$^7$ ........................................... A61K 9/28
(52) U.S. Cl. .................... 424/464; 424/465; 424/474; 424/476; 424/489; 424/479; 424/480; 424/441; 426/285
(58) Field of Search ........................... 424/464, 465, 424/474, 476, 489; 426/285

(56) References Cited

U.S. PATENT DOCUMENTS

| | | |
|---|---|---|
| 4,327,076 | 4/1982 | Puglia et al. . |
| 4,609,543 | 9/1986 | Morris et al. . |
| 4,684,534 | 8/1987 | Valentine . |
| 4,828,845 | 5/1989 | Zamudio-Tena et al. . |
| 5,215,755 | * 6/1993 | Roche et al. .................... 424/480 |
| 5,320,848 | 6/1994 | Geyer et al. . |
| 6,024,981 | 2/2000 | Khankarti et al. . |
| 6,060,078 | 5/2000 | Lee . |

FOREIGN PATENT DOCUMENTS

| | | |
|---|---|---|
| 0 070 127 | 1/1983 | (EP) . |
| 0 192 460 B1 | 8/1986 | (EP) . |
| WO 93/13758 | 7/1993 | (WO) . |
| WO 99/17771 | 4/1999 | (WO) . |

OTHER PUBLICATIONS

Pharmaceutical Dosage Forms: Tablets, 2nd edition, rev.; vol. 2; Leiberman et al., ed.; 1990. pp. 211–217 and 327–329.

* cited by examiner

Primary Examiner—Thurman K. Page
Assistant Examiner—Liliana Di Nola-Baron
(74) Attorney, Agent, or Firm—Sharon H. Hegedus

(57) ABSTRACT

A tablet and process for making the same is provided. The tablet is made from a granular agglomerate comprising a mixture of at least one active ingredient and a binder. The granular agglomerate is heated to melt the binder only at or near its surface, and then cooled, such that the melted binder solidifies into a substantially continuous phase, thereby forming a fused layer on the outside of the tablet.

20 Claims, 1 Drawing Sheet

TABLET AND PROCESS FOR MAKING THE SAME

Figure 1:
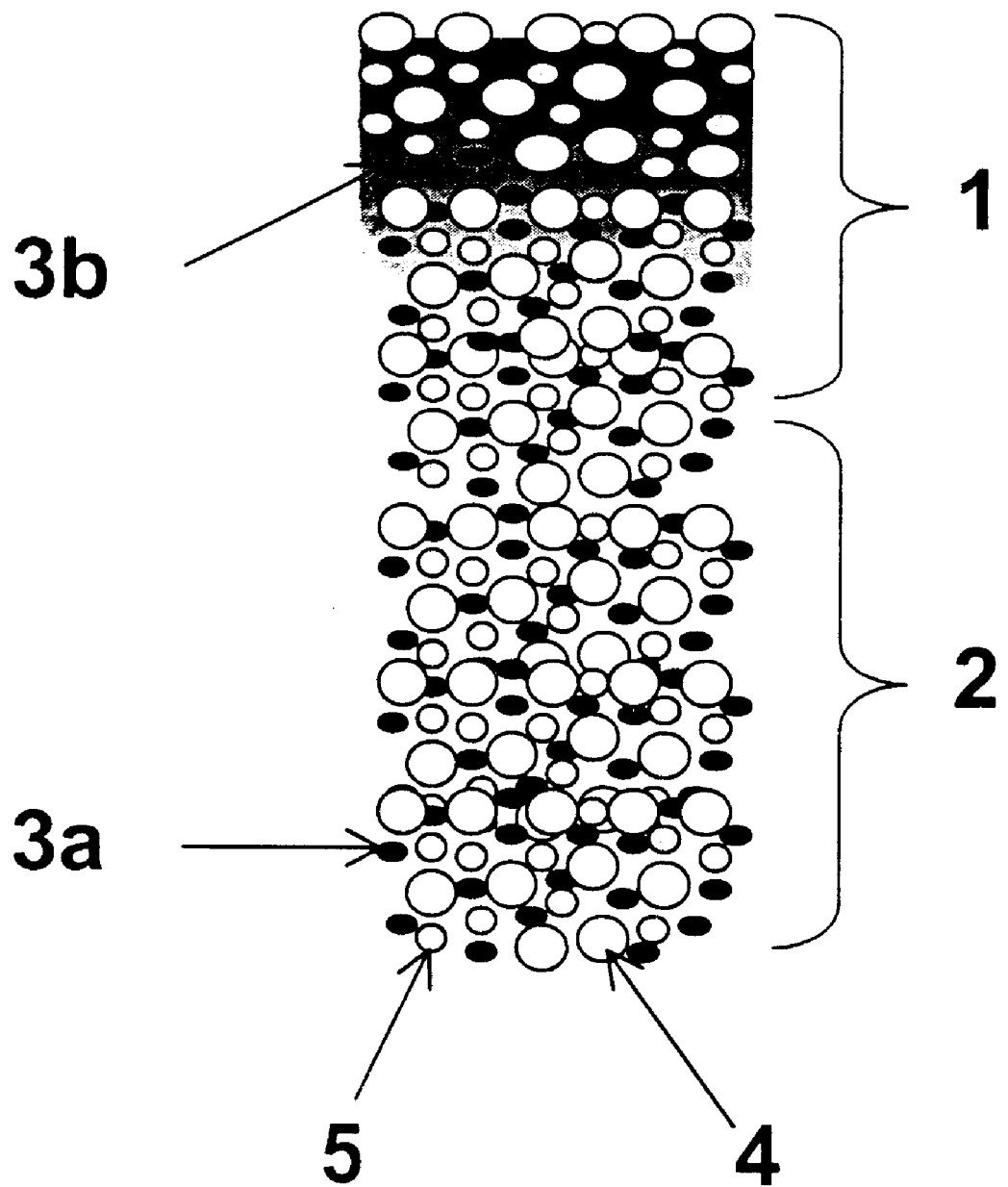

The present invention relates to a tablet having a core/shell configuration made from a mixture comprising at least one active ingredient and a binder.

BACKGROUND OF THE INVENTION

Pharmaceuticals intended for oral administration are typically provided in solid form as tablets, capsules, pills, lozenges, or granules. Tablets are swallowed whole, chewed in the mouth, or dissolved in the oral cavity. Soft tablets that either are chewed or dissolve in the mouth are often employed in the administration of pharmaceuticals where it is impractical to provide a tablet for swallowing whole. With chewable tablets, the act of chewing helps to break Up the tablet particles as the tablet disintegrates and may increase the rate of absorption by the digestive tract. Soft tablets are also advantageous where it is desirable to make an active ingredient available topically in the mouth or throat for both local effects or systemic absorption. Soft tablets are also utilized to improve drug administration in pediatric and geriatric patients. Soft tablets designed to disintegrate in the mouth prior to swallowing are particularly useful for improving compliance of pediatric patients.

Generally, soft tablets are made by compaction of a mixture of tabulating compounds including an active ingredient, flavoring, binders, etc. The mixture is fed into a die cavity of a tablet press and a tablet is formed by applying pressure. Hardness of the resulting tablet is a direct function of the compaction pressure employed and the compatibility oi the ingredients in the formulation. A softer tablet, having an easier bite-through, may be prepared by employing reduced compaction pressures. The resulting tablet is softer, but also more fragile, brittle, and easily chipped.

Soft tablets designed to disintegrate in the mouth without chewing are disclosed by Cousin et al., in U.S. Pat. No. 5,464,632, and Wehling et al., in U.S. Pat. Nos. 5,223,264 and 5,178,878. While these soft tablets for oral administration advantageously disintegrate completely in the mouth prior to swallowing, they have the disadvantage of being highly friable, requiring costly specialized handling and packaging in order to prevent breakage.

Several workers in the field have described chewable tablets comprising an active ingredient and a fatty or polymeric binder material. PCT Application No. WO 93/13758 describes tablets made by combining and compressing a meltable binder, excipients, and a pharmaceutically active ingredient into a tablet, melting the binder in the tablet, and the solidifying the binder. During the melting step, the binder, a material such as a natural fat or polyethylene glycol, flows and fills in minor cracks within the tablet. If a coating is desired on the tablet, it must be coated with a coating material in a separate step.

U.S. Pat. No. 4,684,534 discloses a chewable tablet having a harder outer shell and a softer interior. The tablet is made from agglomerates comprising a carbohydrate and a small amount of a carbohydrate binder such as maltodextrin, in addition to the active ingredient. The agglomerates are compressed into a tablet, resulting in the harder outer shell surrounding the softer interior. The hardness of the outer shell is on the order of 6 to 18 kp.

It has now been discovered that a tablet, preferably a soft tablet, having a core/shell configuration may be made from a mixture comprising at least one active ingredient and a binder having a melting point of about 20 to about 180° C. A granular agglomerate is formed from the mixture, and heated to melt the binder only at or near the surface of the granular agglomerate. The granular agglomerate is then cooled such that the melted binder solidifies into the continuous phase of a fused layer, which surrounds and protects the core of the tablet.

SUMMARY OF THE INVENTION

The invention provides a process for making a tablet comprising a granular agglomerate core and a fused layer surrounding said core, comprising: a) forming a granular agglomerate core from a mixture comprising at least one active ingredient and a binder having a melting point of about 20 to about 180° C.; b) heating the granular agglomerate core at a temperature and for a period of time to melt the binder only at or near the surface of the granular agglomerate core; and c) cooling the granular agglomerate core such that the melted binder solidifies into a substantially continuous phase of said fused layer, as well as a tablet made by such process.

The invention also provides a tablet comprising a granular agglomerate core and a fused layer surrounding said core, wherein said core and said fused layer have the same composition comprising at least one active ingredient and a binder having a melting point of about 20 to about 180° C., and further wherein said binder forms a substantially continuous phase within the fused layer.

BRIEF DESCRIPTION OF THE INVENTION

FIG. 1 is a cross-section of a portion of the surface of a tablet according to the invention.

DETAILED DESCRIPTION OF THE INVENTION

The tablet is made from a mixture comprising one or more active ingredients and one or more binders. Suitable active ingredients include pharmaceuticals, minerals, vitamins and other nutraceuticals. Suitable phannaceuticals include analgesics, decongestants, expectorants, antitussives, antihistamines, gastrointestinal agents, diuretics, bronchodilators, sleep-inducing agents and mixtures thereof. Preferred pharmaceuticals for use as the active ingredient include acetaminophen, ibuprofen, flurbiprofen, naproxen, diclofenac, aspirin, pseudoephedrine, phenylpropanolamine, chlorpheniramine maleate, dextromethorphan, diphenhydramine, famotidine, loperamide, ranitidine, cimetidine, astemizole, terfenadine, fexofenadine, cetirizine, antacids, mixtures thereof and pharmaceutically acceptable salts thereof. More preferably, the active ingredient is selected from the group consisting of acetaminophen, ibuprofen, pseudoephedrine, dextromethorphan, diphenhydramine, chlorpheniramine, calcium carbonate, magnesium hydroxide, magnesium carbonate, magnesium oxide, aluminum hydroxide, mixtures thereof, and pharmaceutically acceptable salts thereof.

The active ingredient(s) are present in the mixture in a therapeutically effective amount, which is an amount that produces the desired therapeutic response upon oral administration and can be readily determined by one skilled in the art. In determining such amounts, the particular compound being administered, the bioavailability characteristics of the active ingredient, the dose regime, the age and weight of the patient, and other factors must be considered.

If the active ingredient has an objectionable taste, it may be coated with a taste masking coating, as known in the art.

Examples of suitable taste masking coatings are described in U.S. Pat. No. 4,851,226, U.S. Pat. No. 5,075,114, and U.S. Pat. No. 5,489,436. Commercially available taste masked active ingredients may also be employed. For example, acetaminophen particles which are encapsulated with ethylcellulose or other polymers by a coaccervation process may be used in the present invention. Coaccervation-encapsulated acetaminophen may be purchased commercially from Eurand America, Inc. Vandalia, Ohio, or from Circa Inc., Dayton, Ohio.

The binder is a thermoplastic material having a melting point in the range of about 20 to about 180° C., preferably about 40 to about 140° C., more preferably about 55 to about 100° C. Examples of suitable binders include fats such as cocoa butter, hydrogenated vegetable oil Such as palm kernel oil, cottonseed oil, sunflower oil, and soybean oil, mono, di, and triglycerides, phospholipids, waxes such as Carnauba wax, spermaceti wax, beeswax, candelilla wax, shellac wax, microcrystalline wax, and paraffin wax, water soluble polymers such as polyethylene glycol, polyethylene oxides and derivatives, and sucrose esters. Preferably, the binder is selected from hydrogenated vegetable oil, polyethylene glycol, waxes, and mixtures thereof.

The amount of binder present in the mixture is up to about 20 weight percent of the mixture, preferably up to about 10 weight percent of the mixture, more preferably up to about 5 weight percent of the mixture.

The mixture may contain other conventional ingredients, such as fillers, which include water-soluble compressible carbohydrates such as dextrose, sucrose, mannitol, sorbitol, maltitol, xylitol, lactose, and mixtures thereof; conventional dry binders like cellulose, cellulosic derivatives, polyvinyl pyrrolidone, starch, modified starch, and mixtures thereof, and in particular microcrystalline cellulose; sweeteners like aspartame, acesulfame potassium, sucralose and saccharin; and lubricants, such as magnesium stearate, stearic acid, talc, and waxes. The mixture may also incorporate pharmaceutically acceptable adjuvants, including, for example, preservatives, flavors, antioxidants, surfactants, and coloring agents.

The mixture of active ingredient, binder, and any optional ingredients is formed into a granular agglomerate. This may be done by any method, including for example using compacting roller technology such as a chilsonator or drop roller, or by molding, casting, or extrusion technologies. Preferably, the granular agglomerate is formed by compaction using a rotary tablet press as known in the art. In a rotary tablet press, a metered volume of powder is filled into a die cavity, which rotates as part of a "die table" from the filling position to a compaction position where the powder is compacted between an upper and a lower punch to an ejection position where the resulting tablet is pushed from the die cavity by the lower punch and guided to an ejection chute by a stationary "take-off" bar.

Preferably, the granular agglomerate is prepared such that the tablet is relatively soft, i.e., capable of dissolving in the mouth or being chewed. The hardness of the tablet is preferably up to about 15 kiloponds per square centimeter ($kp/cm^2$). More preferably, the hardness of the tablet is in the range of about 1 to about 8, most preferably about 2 to about 5, $kp/cm^2$. Hardness is a term used in the art to describe the diametral breaking trength as measured by conventional pharmaceutical hardness testing equipment, such as a Schicuniger Hardness Tester. In order to compare values across different size tablets, the breaking strength must be normalized for the area of the break. This normalized value, expressed in $kp/cm^2$, is sometimes referred in the art as tablet tensile strength. A general discussion of tablet hardness testing is found in Leiberman et al., *Pharmaceutical Dosage Forms—Tablets*, Volume 2, $2^{nd}$ cd., Marcel Dekker Inc., 1990, pp. 213–217, 327—329.

Next, the granular agglomerate is heated to a temperature and for a period of time to melt the binder only at or near the surface of the granular agglomerate, preferably to a depth in the tablet core of about 0.1 to about 2.0 mm from the surface. It is critical during heating that binder below the surface of the granular agglomerate remain in the solid phase. In this manner, melted binder at the surface of the granular agglomerate flows to form the continuous phase of a fused layer. Inside, the tablet core remains solid and maintains its physical properties, including hardness. The temperature of the tablet surface during the heating step should be above the melting point of the binder, but below the melting points and the decomposition temperatures of the other ingredients of the tablet, including the active ingredient. Accordingly, the temperature during heating is typically in the range of about 30 to about 200° C. The time of heating should be minimal, i.e., on the order of less than about 30 seconds, more preferably less than about 15 seconds, to ensure that only binder at or near the surface of the granular agglomerate melts. Suitable heat sources include a radiant heater or laser.

The temperature and time of cooling are such as to solidify the melted binder. Typically, the temperature during cooling is about 25 to about 0° C., and the time of cooling is about 10 to about 60 seconds.

Advantageously, the fused layer forms a protective coating without the need for the separate application of coating materials. The fused layer and the core of the tablet have substantially the same composition, that is they both comprise the active ingredient, the binder, and any other optional ingredients in the same amounts and ratios. The tablet has improved friability compared with a conventional tablet made from a granular agglomerate containing the same ingredients and formed in the same manner, but not heated and cooled to form the fused layer according to the invention. Whereas the friability of the conventional, untreated tablet will be typically greater than 2%, i.e., 2–10%, the friability of tablets made according to the invention will be typically less than 2%, i.e., 0–0.75%. A discussion of tablet friability is presented in USP 23 (1995) <1216>p. 1981. Such improved friability allows for greater flexibility in subsequent processing and handling of the tablet.

Moreover, since the tablet of the invention may be compressed to a lower hardness under reduced pressures because it benefits from the protection of the fused layer, the incidence of fracturing any taste masking coating on the particles of the active ingredient is reduced. The tablet of the present invention therefore provides the superior taste masking of a soft tablet, while maintaining the robustness to handling, shipping, and packaging procedures previously only realized by harder tablets.

FIG. 1 shows a cross-sectional view of a portion of a tablet according to the invention. The tablet comprises a granular agglomerate core 2 beneath a fused layer 1. The core 2 is formed of solid granules of binder 3a, active ingredient 4 and an optional ingredient 5. The fused layer 1 contains solid granules of active ingredient 4 and optional ingredient 5, as well as a continuous phase 3b of binder.

Conventional outer coatings may be applied to the tablet if desired. As an added advantage, the fused outer layer serves as a barrier to protect the tablet core from damage by solvents used during conventional outer coating processes.

Such outer coatings comprise one or more conventional tablet coating materials, such as isomalt, monosaccharides, disaccharides, polysaccharides, cellulose derivatives, shellacs, polyhedric alcohols such as xylitol, mannitol, sorbitol, maltitol, erythlitol, and the like. A variety of such outer coatings are known in the art, and any of these may be employed using techniques also known in the art.

Specific embodiments of the present invention are illustrated by way of the following examples. This invention is not confined to the specific limitations set forth in these examples, but rather to the scope of the appended claims. Unless otherwise stated, the percentages and ratios given below are by weight.

EXAMPLE

Chewable tablets according to the invention and comparative tablets were made as follows and then evaluated for friability.

For both the tablets according to the invention and the comparative tablets, the following ingredients were blended, as solids, in the ratios listed until visually uniform:

46.3% Coated Acetaminophen (90% acetaminophen)
6.25% Polyethylene Glycol 8000
0.65% Aspartame
5.2% Crospovidone
2.1% Alginic Acid
0.65% Sodium Bicarbonate
0.65% Flavor
0.65% Citric Acid Anhydrous Powder
37.1% Dextrates The following additional ingredient was added to the mixture, which was again blended until visually uniform:

0.43% Magnesium Stearate

Tablets were then made by compacting this mixture on a tablet press using 19/32" tooling to a hardness of 1 to 3 kp, and a target tablet weight of approximately 1200 mg.

The tablets according to the invention were exposed to a radiant heater set at 500° C. for 10 seconds per side. The tablets were then cooled to room temperature. The comparative tablets were not heated.

The tablets were evaluated for friability using the apparatus described in USP 23 (1995) <1216>Tablet Friability, p. 1981. Tablets were evaluated after 100 drops in 4 minutes. One hundred percent of the comparative tablets were broken after 40 revolutions, while none of the tablets heated according to the invention for 10 seconds per side were broken after 100 revolutions.

We claim:

1. A process for making a tablet comprising a granular agglomerate core and a fused layer surrounding said core, comprising:
   a) forming a granular agglomerate core from a mixture comprising at least one active ingredient and a binder having a melting point of about 20 to about 180° C.;
   b) heating the granular agglomerate core at a temperature and for a period of time to melt the binder only at or near the surface of the granular agglomerate core; and
   c) cooling the granular agglomerate core such that the melted binder solidifies into a substantially continuous phase of said fused layer.

2. The process of claim 1, wherein said tablet has a hardness of up to about 20 kp/cm$^2$.

3. The process of claim 1, wherein said binder is selected from the group consisting of fats, waxes, water soluble polymers, long chain alcohols and their derivatives, and mixtures thereof.

4. The process of claim 3, wherein said binder is selected from the group consisting of hydrogenated vegetable oil, polyethylene glycol, waxes, and mixtures thereof.

5. The process of claim 1, wherein said active ingredient is selected from the group consisting of acetaminophen, ibuprofen, pseudoephedrine, dextromethorphan, diphenhydramine, chlorpheniramine, calcium carbonate, magnesium hydroxide, magnesium carbonate, magnesium oxide, aluminum hydroxide, mixtures thereof, and pharmaceutically acceptable salts thereof.

6. The process of claim 1, wherein said fused layer has a thickness of about 0.01 to about 2 mm.

7. The process of claim 1, wherein said binder comprises less than 20 weight percent of the granular agglomerate.

8. The process of claim 1, where the granular agglomerate is fonned by rotary compaction.

9. The process of claim 1, further comprising applying at least one outer coating over the fused layer.

10. A tablet made by the process of claim 1.

11. The tablet of claim 10, wherein the binder is selected from the group consisting of hydrogenated vegetable oil, polyethylene glycol, waxes, long chain alcohols and their derivatives and mixtures thereof, and the active ingredient is selected from the group consisting of acetaminophen, ibuprofen, pseudoephedrine, dextromethorphan, diphenhydramine, chlorpheniramine, calcium carbonate, magnesium hydroxide, carbonate, or oxide, aluminum hydroxide, mixtures thereof, and pharmaceutically acceptable salts thereof.

12. A tablet comprising a granular agglomerate core and a fused layer surrounding said core, wherein said core and said fused layer have the same composition comprising at least one active ingredient and a binder having a melting point of about 20 to about 180° C., and further wherein said binder forms a substantially continuous phase within said fused layer.

13. The tablet of claim 12 having a hardness of up to about 20 kp/Cm$^2$.

14. The tablet of claim 12, wherein said binder is selected from the group consisting of fats, waxes, water soluble polymers, long chain alcohols and their derivatives, and mixtures thereof.

15. The tablet of claim 14, wherein said binder is selected from the group consisting of hydrogenated vegetable oil, polyethylene glycol, waxes, and mixtures thereof.

16. The tablet of claim 12, wherein said active ingredient is selected from the group consisting of acetaminophen, ibuprofen, pseudoephedrine, dextromethorphan, diphenhydramine, chlorpheniramine, calcium carbonate, magnesium hydroxide, magnesium carbonate, magnesium oxide, aluminum hydroxide, mixtures thereof, and pharmaceutically acceptable salts thereof.

17. The tablet of claim 12, wherein said fused layer has a thickness of about 0.01 to about 2 mm.

18. The tablet of claim 12 further comprising at least one outer coating disposed over the fused layer.

19. The tablet of claim 12 wherein the friability of said tablet is less than about 2.0%.

20. The tablet of claim 12 wherein the friability of said tablet is less than about 0.75%.

* * * * *